(12) United States Patent
Yan

(10) Patent No.: US 9,829,424 B2
(45) Date of Patent: Nov. 28, 2017

(54) SHEATH FLOW DEVICE FOR EVAPORATION LIGHT SCATTERING DETECTOR

(71) Applicant: Chao Yan, Shanghai (CN)

(72) Inventor: Chao Yan, Shanghai (CN)

( * ) Notice: Subject to any disclaimer, the term of this patent is extended or adjusted under 35 U.S.C. 154(b) by 0 days.

(21) Appl. No.: 15/036,416

(22) PCT Filed: Aug. 27, 2015

(86) PCT No.: PCT/CN2015/088313
§ 371 (c)(1),
(2) Date: May 13, 2016

(87) PCT Pub. No.: WO2016/029866
PCT Pub. Date: Mar. 3, 2016

(65) Prior Publication Data
US 2016/0290914 A1    Oct. 6, 2016

(30) Foreign Application Priority Data

Aug. 29, 2014 (CN) .......................... 2014 1 0437831

(51) Int. Cl.
*G01N 15/14* (2006.01)
*G01N 1/40* (2006.01)
(Continued)

(52) U.S. Cl.
CPC ....... *G01N 15/1404* (2013.01); *G01N 1/4022* (2013.01); *G01N 15/1459* (2013.01);
(Continued)

(58) Field of Classification Search
CPC ............ G01N 15/1404; G01N 1/4022; G01N 5/1484; G01N 15/1459; G01N 2001/4027;
(Continued)

(56) References Cited

U.S. PATENT DOCUMENTS 4,958,529 A * 9/1990 Vestal ................ G01N 30/7273
250/288
6,473,171 B1 * 10/2002 Buttry .................... G01N 15/14
356/246

(Continued)

*Primary Examiner* — Sang Nguyen

(57) ABSTRACT

A sheath flow device for an evaporation light scattering detector comprises an evaporation pipe fastener (110), an evaporation pipe heat insulating component (120), a sheath flow nozzle blocking plate (130), a sheath flow nozzle (140), a sheath flow sleeve (150), a sheath flow outlet piece (170) and a stainless steel spray needle (160). The evaporation pipe fastener, the evaporation pipe heat insulating component, the sheath flow nozzle blocking plate, the sheath flow nozzle, the sheath flow sleeve and the sheath flow outlet piece are concentrically connected orderly from front to back, and all provided with concentric inner holes. Said device is applicable to ELSD sheath flow devices ranging from nanoliter-scale to microliter-scale. On one hand, material particles entering a testing pool are enveloped and aggregated so that the formation of eddy and turbulence can be reduced, the chromatographic peak shape of a sample can be improved and the stability of sample detection can be enhanced; on the other hand, the testing pool can be cleaned so that baseline noise can be reduced and the signal to noise ratio can be increased.

6 Claims, 3 Drawing Sheets

(51) Int. Cl.
   *G01N 30/74* (2006.01)
   *G01N 30/84* (2006.01)
(52) U.S. Cl.
   CPC ......... *G01N 15/1484* (2013.01); *G01N 30/74* (2013.01); *G01N 30/84* (2013.01); *G01N 2001/4027* (2013.01); *G01N 2015/1409* (2013.01); *G01N 2030/8494* (2013.01)
(58) Field of Classification Search
   CPC . G01N 2015/1409; G01N 21/47; G01N 30/74
   See application file for complete search history.

(56) References Cited

U.S. PATENT DOCUMENTS

| | | | | |
|---|---|---|---|---|
| 7,468,789 | B2* | 12/2008 | Czarnek | G01N 15/1404 356/244 |
| 2001/0001575 | A1* | 5/2001 | Anderson, Jr. | G01N 27/44721 356/337 |
| 2006/0238744 | A1* | 10/2006 | O'Donohue | G01N 30/74 356/37 |
| 2011/0181880 | A1* | 7/2011 | Saari-Nordhaus | G01N 30/74 356/337 |

\* cited by examiner

SHEATH FLOW DEVICE FOR EVAPORATION LIGHT SCATTERING DETECTOR

BACKGROUND OF THE INVENTION

This invention is concerned with evaporative light scattering detector (ELSD), especially concerned with a sheath-flow device for ELSD.

ELSD is a universal and mass sensitive detector. It is not susceptible to molecular structure and spectroscopic properties of a compound. ELSD is suitable for detection of any compounds that have a lower volatility than the mobile phase, therefore, it can be used for volatile and semi-volatile compounds, especially suitable and powerful for detection and analysis of natural product, traditional Chinese medicine (TCM), lipid, surfactant and hydrocarbon, etc. Since ELSD has little effect on the peak broadening of micro-flow chromatography, it is suitable for any chromatographic techniques based on capillary column.

Micro-fluid evaporative light-scattering detector (pELSD) is a miniaturized device that matches nano-liter to micro-liter/min flow of the mobile phase in a capillary chromatographic system. Its principle is as follows: 1) the effluent from the capillary column is nebulized into an aerosol, then, 2) the solvent in the aerosol is evaporated and the solute is left as tiny particles, then, 3) the particles gets into the detection cell where they scatter the photos from the light beam, and then, 4) a photomultiplier detects the photos and convert the optical signal into an electronic signal.

Because of the extremely low flow rate of the capillary column, the quantity of the solute compounds after nebulization and evaporation into the detection cell is very low and easy to spread, and resulting in low detection sensitivity and low stability. In addition, the low flow rate of the small amount of solute aerosol is susceptible to form eddy and turbulence flow, resulting in un-symmetric chromatographic peak.

Sheath flow is an auxiliary flow that can be either sheath liquid or sheath gas flow. The essence of the sheath-flow is to focus the effluent, which is similar to the sheath flow used in cytometer to avoid blood cell to bypass the counter.

There is a sheath flow device in conventional ELSD but it is not feasible to be used in pELSD in which the flow is only a few microliters/min. The conventional sheath flow device is not able to prevent heat transform to the detection cell from the evaporative tube.

BRIEF SUMMARY OF THE INVENTION

Therefore, dealing with the above mentioned problems, we invent a sheath flow device for μELSD. The technical scheme is as follows:

A sheath flow device for ESLD includes a fixing base for evaporating tube, heat insulating part for evaporating tube, a sheath flow baffle, a sheath flow nozzle, a sheath flow sleeve, a sheath flow outlet, and a stainless steel needle of nozzle. The above mentioned six parts have the same internal diameter and are concentrically connected according to the mentioned order. The inner-bore of the fixing base for evaporating tube and the heat insulating part for evaporating tube is equal to the external diameter of evaporating tube in ELSD. The inner-bore entry end of the sheath flow baffle has a step washer which has the same inner diameter as the external diameter of evaporating tube. The inner-bore of the said sheath flow nozzle is wide in the front and narrow in the back like a trumpet shape. The inner-diameter of the inlet of the sheath flow nozzle is as same as the inner-diameter of the sheath flow baffle's exit end and the inner-diameter of the outlet of the sheath flow nozzle is equal to the inner-diameter of the stainless steel needle. And there is a sheath gas entry across connected with its inner-bore of sheath gas sleeve. The front end of the stainless steel needle is welded to the outlet of sheath gas nozzle and the back end of the stainless steel needle is introduced into the inter-diameter of the hole in the outlet sheet passed through the sheath gas sleeve, meanwhile, flushed with the exit end of the sheath flow outlet. The inner diameter of the sheath flow outlet is approximately above the external diameter of the stainless steel needle, and it formed the sheath gas where it passed through the circular orifice between the outside-diameter of the stainless steel tube and the inside-diameter of the hole in the outlet sheet.

All the said fixing base for evaporating tube, heat insulating part for evaporating tube, sheath flow baffle and sheath flow nozzle are cylinders with the same external diameter. And the fixing base for evaporating tube, heat insulating part for evaporating tube, sheath flow baffle and the sheath flow nozzle are concentrically connected by fixed bolt. And the sheath flow nozzle also is concentrically connected with the sheath flow sleeve by fixed bolt.

There is a groove fit with the sheath flow outlet, in the back of a sheath flow sleeve. And the groove is concentrically connected with the sheath flow sleeve. The sheath flow outlet is fixed in the groove.

The inner-bore of the mentioned sheath flow sleeve presents a scalariform range from the wide diameter in the front to the narrow diameter in the back.

The sheath gas flow passage is vertical to the inner-bore of the sheath flow sleeve when enters the gas flow passage.

The said sheath flow outlet is removable and fixed in the mentioned groove.

The said heat insulating part for evaporating tube is made up of three layers of heat insulating materials.

The said heat insulating part for evaporating tube is made up of plastic layer, veneer layer and rubber spacer.

The inner diameter of the stainless steel needle of nozzle is equal to 1 to 5 millimeter and the external diameter is 2 to 6 millimeter.

There is a seal ring respectively between the said heat insulating part for evaporating tube and sheath flow baffle, the sheath flow baffle and sheath flow nozzle, the sheath flow nozzle and sheath flow sleeve.

This invented sheath flow device of ELSD has the following advantages:

Firstly, this invention achieved effective heat insulation between the evaporating tube and the detection cell, so that it can prevent the excessive evaporation of aerosols, and meanwhile decrease the heat effect to the detection cell from the evaporating temperature.

Secondly, the sheath gas can effectively achieved the parcel and convergence for the micro particles, which can make sure the detection beam get into the center of the sample particles flow. And this could increase the detective sensitivity and stability and also improve the shape of chromatographic peak.

Thirdly, the invented device can effectively control the sheath parameters and ensure the best experimental conditions through a removable sheath flow outlet.

Fourthly, in the present device, the sheath gas can clean the cavity of detection cell, and effectively decrease the noise of the baseline, and increasing the signal to noise ratio of the ELSD detector.

DETAILED DESCRIPTION OF THE INVENTION

Figure 1:
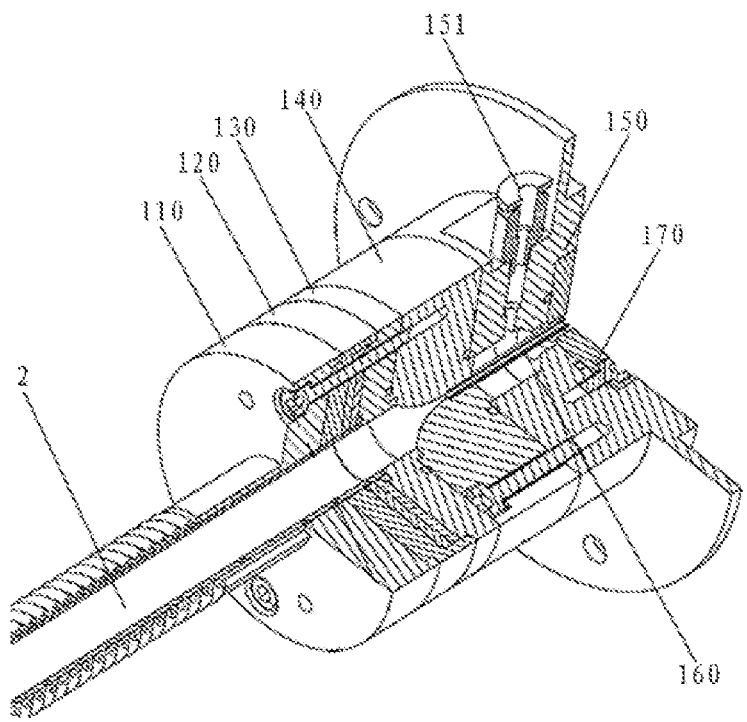
FIG. 1 is a structural schematic diagram of the sheath-flow device for ELSD
Figure 2:
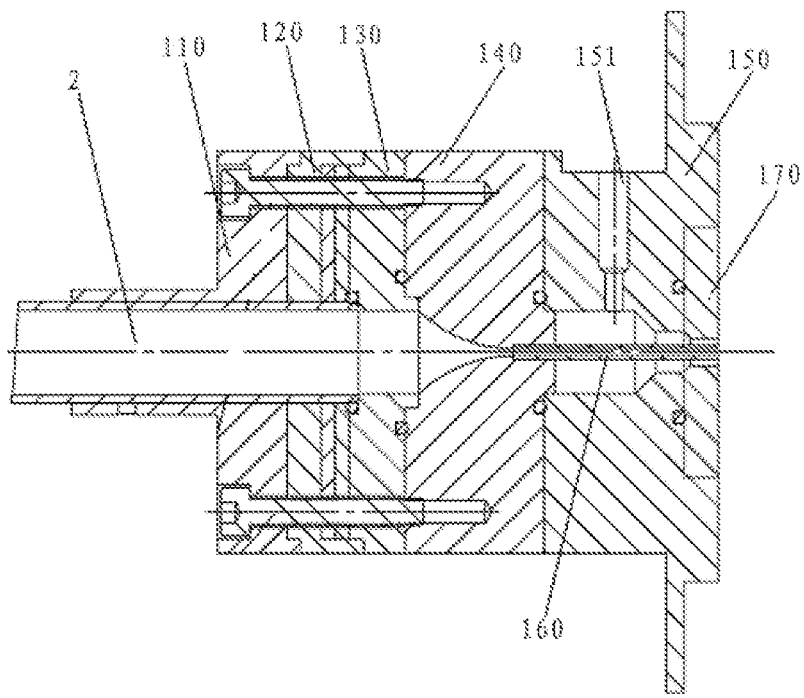
FIG. 2 is a section structure diagram of the sheath-flow device for ELSD

As shown in FIG. 1 and FIG. 2, a sheath flow device for ESLD which includes a fixing base for evaporating tube 110, a heat insulating part for evaporating tube 120, a sheath flow baffle 130, a sheath flow nozzle 140, a sheath flow sleeve 150 and a sheath flow outlet 170. The above mentioned six parts have the same internal diameter and are concentrically connected according to the mentioned order.

Thereinto, there is a seal ring respectively between the said heat insulating part for evaporating tube 120 and sheath flow baffle 130, the sheath flow baffle 130 and sheath flow nozzle 140, the sheath flow nozzle 140 and sheath flow sleeve 150.

All the said fixing base for evaporating tube 110, heat insulating part for evaporating tube 120, sheath flow baffle 130 and sheath flow nozzle 140 are cylinders with the same external diameter.

And the fixing base for evaporating tube 110, heat insulating part for evaporating tube 120, sheath flow baffle 130 and the sheath flow nozzle 140 are concentrically connected by fixed bolts. And the sheath flow nozzle 140 also is concentrically connected with the sheath flow sleeve 150 by a fixed bolt. And there is a groove fit with the sheath flow outlet 170, in the back of a sheath flow sleeve 150. And the groove is concentrically connected with the sheath flow sleeve 150. The sheath flow outlet 170 is fixed in the groove.

The sheath flow outlet 170 is removable and fixed in the mentioned groove, and changing the sheath flow outlet 170 can match different stainless steel needle of nozzle 160 of different external diameters.

The inner-bore of fixing base for evaporating tube 110 and the heat insulating part for evaporating tube 120 is the same as the external diameter of evaporating tube 2 in ELSD.

Heat insulating part for evaporating tube 120 achieved effective heat insulation between the evaporating tube 2 and the detection cell, so that it can prevent the excessive evaporation of aerosols, and meanwhile decrease the effect to the detection cell bring from the evaporating temperature. The said heat insulating part for evaporating tube is made up of three layers of heat insulating materials plastic layer, veneer layer and rubber spacer.

The inner-bore entry end of the sheath flow baffle has a step washer, and its diameter is as same as the external diameter of evaporating tube 2.

The inner-bore of the said sheath flow nozzle 140 is wide in the front and narrow in the back like a trumpet shape. The entry end inner-bore of the sheath flow nozzle 140 is as same as the external diameter of the sheath flow baffle 130's inner-bore exit end and the exit end inner-bore is equal to the inner diameter of the stainless steel needle of nozzle 160.

And there is an entry across 151 of sheath gas connected with its inner-bore on the sheath flow sleeve 150. The sheath gas can clean the cavity of detection cell, and effectively decrease the noise of the baseline, and increasing the signal to noise ratio of the ELSD detector.

The entry across 151 of sheath gas is vertical to the inner-bore of sheath flow sleeve 150.

Thereinto, the inner-bore of the mentioned sheath flow sleeve 150 presents a scalariform range from the wide band in the front to the narrow band in the back.

The front end of the stainless steel needle of nozzle 160 is inserted into the exit end of sheath flow nozzle 140 inner-bore and the back end of the stainless steel needle of nozzle 160 thread the inner-bore of sheath flow sleeve 150 and insert into the inner-bore of sheath flow outlet 170, meanwhile, flush the exit end of the sheath flow outlet 170.

The inner diameter of the sheath flow outlet 170 is slightly bigger than the external diameter of the stainless steel needle of nozzle 160. An exit annulus is formed between the inner diameter of the sheath flow outlet 170 and the external diameter of the stainless steel needle of nozzle 160. The exit annulus can effectively control the sheath parameters and ensure the best experimental conditions through a removable sheath flow outlet. And changing the sheath flow outlet 170 can match different external diameters of different stainless steel needle of nozzle 160, and this can form various annulus conditions.

The inner diameter of the stainless steel needle of nozzle is equal to 1 to 5 millimeter and the external diameter is 2 to 6 millimeter.

Operation Procedure of this Invention

The effluent (including sample and solvents) from the capillary column is nebulized into an aerosol and then, gets into the evaporating tube 2. When the aerosol moves in the evaporating tube 2, the solvent in the aerosol is evaporated and the solute is left as tiny particles, then the particles gets into the detection cell where they scatter the photos from the light beam and then, a photomultiplier detects the photos and converts the optical signal into an electronic signal. Heat from evaporation tube 2 firstly is prevented by heat insulating part for evaporating tube 120, and the sample particles flow through the sheath flow baffle 130 and the stainless steel needle of nozzle 160. Meanwhile, the sheath gas (pure air or nitrogen) get into inner-bore of the sheath flow sleeve 150 by the entry across of sheath gas 151 on the sheath flow sleeve 150. And then the sheath gas will get into the detection cell across the outlet annulus made up of the stainless steel needle of nozzle 160 and sheath flow outlet 170 and the sheath gas simultaneously enclose and converge the sample particles runout of the stainless steel needle of nozzle 160. And the enclosed and converged sample particles encounter the light beam from the light source and scatter the photos, and the light scattering signal is collected by detecting module (usually a photomultiplier tube), and transform the electronic signal to the computer, the resulting in digital data, and then convert into chromatogram. The sheath gas can effectively focus the aerosols, making sure the detection beam get into the center of the flow-pass of the sample particles. And this can increase the detective sensitivity and also improve the shape of chromatographic peak In order to verify the effectiveness of sheath flow device to ELSD in this invention, following experiments were conducted in the present sample:

The present experiment is the detection of glucose by ELSD.

Experiment Condition:

Atomization carrier gas (high purity nitrogen) flow: 0.4 L/min;

Atomization carrier gas pressure: 5.40 bar;

Evaporation tube size: 12 mm I.D.*25 cm length;
Evaporating temperature: 30° C.;
Mobile phase: pure water;
column flow rate: 900 nL/min;
Sample: $1\times10^{-2}$ g/mL of glucose;
Sample size: 20 nL;
Sheath flow rate: 0-3.0 L/min.

Figure 3:
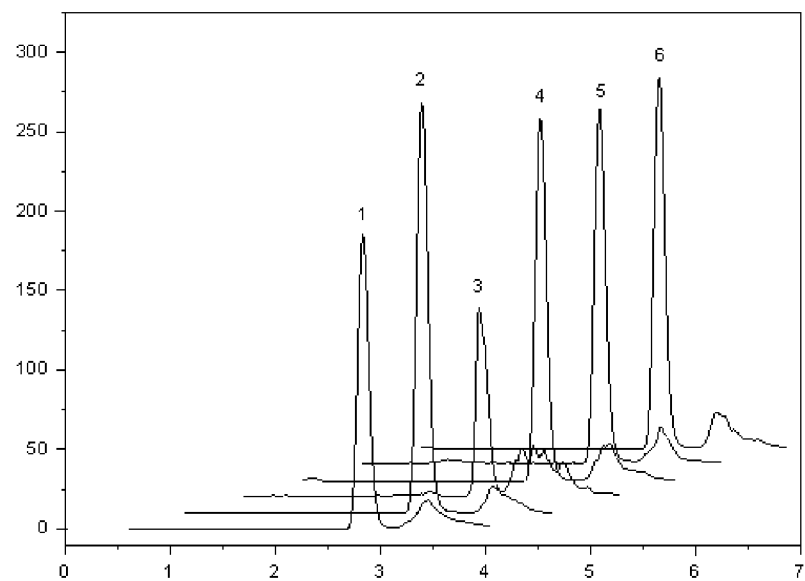
FIG. 3 is an experimental chromatogram before installing the sheath-flow device

As shown in FIG. 3, when the ELSD was directly connected with the detection cell and not installed with a sheath flow device, chromatographic peaks of glucose appear trail and bump, and the RSDs of peak area and peak height for six-time continuously sampling are separately 23.41% and 23.76%. The repeatability of both peak area and peak height is poor.

Figure 4:
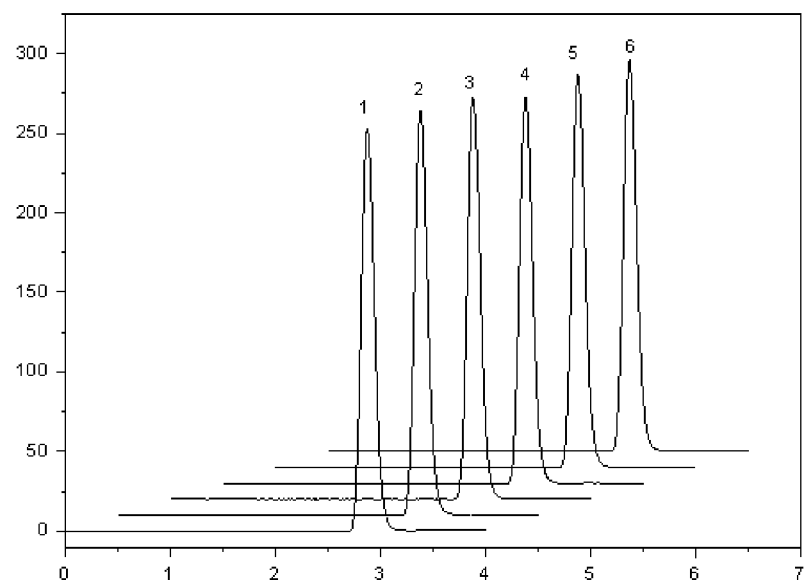
FIG. 4 is an experimental chromatogram after installing the invented sheath-flow device

As shown in FIG. 4, when the ELSD was installed with a sheath flow device with the sheath flow rate of 1.0 L/min, the chromatographic peaks eliminated the phenomenon of trail and bump. And RSDs of peak area and peak height for six-time sampling are separately 1.8% and 1.89%, which demonstrates that the repeatability and precision have been improved significantly.

Figure 5:
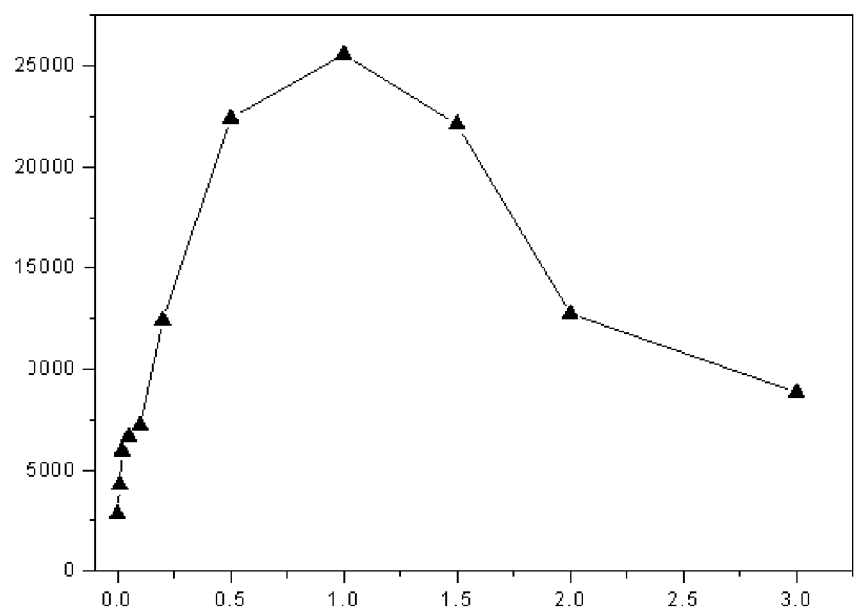
FIG. 5 is a flow chart of signal-to-noise (S/N) ratio with the range of sheath flow

FIG. 5 showed the flow chart of signal-to-noise (S/N) ratio with the range of sheath flow rate. It demonstrates that the sheath flow device can significantly improve the S/N ratio and there exists the best sheath flow condition.

The claimed scope of the present invention is not limited to the embodiments described above, but also should include other obvious changes and alternatives.

What we claimed is:

1. A sheath flow device for evaporative light scattering detector (ESLD), comprising a fixing base, a heat insulating part, a sheath flow baffle, a sheath flow nozzle, a sheath flow sleeve, a sheath flow outlet, and a stainless steel needle; the fixing base, the heat insulating part, the sheath flow baffle, the sheath flow nozzle, the sheath flow sleeve and the sheath flow outlet all have a same internal diameter and are sequentially and concentrically connected; the fixing base, the heat insulating part, the sheath flow baffle and the sheath flow nozzle are concentrically connected by fixed bolts; the sheath flow nozzle is also concentrically connected with the sheath flow sleeve by a fixed bolt; a back side of the sheath flow sleeve comprises a groove concentrically positioned with respect to the sheath flow sleeve, and the sheath flow outlet is fixed in the groove; an inner-bore of the fixing base and an inner-bore of the heat insulating part are each equal to an external diameter of an evaporating tube in the ELSD; an inner-bore entry end of the sheath flow baffle comprises a step washer which has a same inner diameter as the external diameter of the evaporating tube; an inner-bore of the sheath flow nozzle has a reducing diameter from a front part of the sheath flow nozzle to a back part of the sheath flow nozzle; an inner-diameter of an inlet of the sheath flow nozzle is the same as an inner-diameter of an exit of the sheath flow baffle; an inner-diameter of an outlet of the sheath flow nozzle is equal to an inner-diameter of the stainless steel needle; a sheath gas entry channel is connected with an inner-bore of the sheath flow sleeve; a front end of the stainless steel needle is welded to the outlet of the sheath flow nozzle and a back end of the stainless steel needle is introduced into the inner-bore of the sheath flow sleeve and inserted into an inner-bore of the sheath flow outlet and flushed with an exit end of the sheath flow outlet; an inner diameter of the sheath flow outlet is larger than an external diameter of the stainless steel needle so that an exit annulus allowing sheath gas to pass through is formed between the inner diameter of the sheath flow outlet and the external diameter of the stainless steel needle.

2. The sheath flow device for ESLD of claim 1, wherein the fixing base, the heat insulating part, the sheath flow baffle and the sheath flow nozzle are cylinders with a same external diameter.

3. The sheath flow device for ESLD of claim 1, wherein the sheath flow outlet is removable from the groove.

4. The sheath flow device for ESLD of claim 3, wherein the heat insulating part is made of three layers of heat insulating materials.

5. The sheath flow device for ESLD of claim 4, wherein the three layers of heat insulating materials are plastic layer, veneer layer and rubber spacer respectively.

6. The sheath flow device for ESLD of claim 5, wherein the inner diameter of the stainless steel needle is 1 to 5 millimeter and the external diameter of the stainless steel needle is 2 to 6 millimeter.

* * * * *